(12) United States Patent
Cavallaro

(10) Patent No.: US 10,688,042 B1
(45) Date of Patent: Jun. 23, 2020

(54) TOPICAL GEL FOR ALLEVIATING FOOD CRAVINGS AND METHOD OF MAKING SAME

(71) Applicant: Antonino Cavallaro, Miami, FL (US)

(72) Inventor: Antonino Cavallaro, Miami, FL (US)

(*) Notice: Subject to any disclaimer, the term of this patent is extended or adjusted under 35 U.S.C. 154(b) by 0 days.

(21) Appl. No.: 16/653,613

(22) Filed: Oct. 15, 2019

(51) Int. Cl.
*A61K 9/00* (2006.01)
*A61K 47/10* (2017.01)

(52) U.S. Cl.
CPC .......... *A61K 9/0014* (2013.01); *A61K 47/10* (2013.01); *A61K 2800/20* (2013.01)

(58) Field of Classification Search
None
See application file for complete search history.

(56) References Cited

U.S. PATENT DOCUMENTS

| 2007/0270496 A1* | 11/2007 | Della Valle | A61K 31/7032 514/563 |
| 2009/0280074 A1* | 11/2009 | Gschwind | A61K 8/37 424/59 |
| 2016/0081976 A1* | 3/2016 | Bromley | A61K 31/4745 424/456 |

* cited by examiner

*Primary Examiner* — Jennifer A Berrios
(74) *Attorney, Agent, or Firm* — Mark Terry

(57) ABSTRACT

A gel for topical application for alleviating food cravings is disclosed, which includes the steps of: periodically applying a gel topically to a user's skin, wherein said gel comprises: about 45.0 percent by weight of deionized water; about 10.0 percent by weight of benzyl alcohol; about 40.0 percent by weight of ethyl alcohol; about 0.2 percent by weight of tocopherol acetate; about 0.15 percent by weight of docosahexaenoic acid (DHA); about 1.15 percent by weight of resveratrol; about 1.0 percent by weight of a cross-linked polyacrylic acid copolymer; about 0.1 percent by weight of ethylenediaminetetraacetic acid (EDTA); about 200 µL of lemon essential oil; and, from about 100 µL to 200 µL of triethanolamine.

12 Claims, 12 Drawing Sheets

PRIOR ART
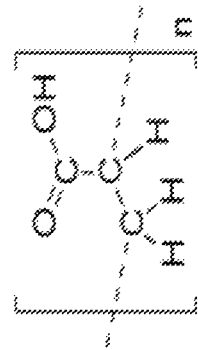
Polyacrylic acid
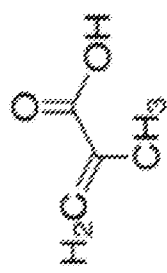
Metacrylic acid
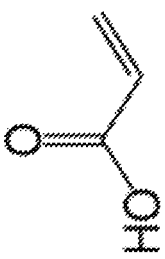
Acrylic acid
200
FIG. 2

PRIOR ART

300

400

| Physical property | Value |
|---|---|
| Viscosity (mPa.s) | 6,000 - 14,000 |
| pH | 5.5 ~ 6 |
| Yield value (dyn/cm2) (initial resistance to flow under stress, yield stress) | 1000 - 2000 |
| Turbidity (NTU, Nephelometric Turbidity Units) | < 20 |
| Stability | Passed 3 months to 45 C, 5 cycles freeze/thaw |

FIG. 11

TOPICAL GEL FOR ALLEVIATING FOOD CRAVINGS AND METHOD OF MAKING SAME

CROSS-REFERENCE TO RELATED APPLICATIONS

Not Applicable.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

TECHNICAL FIELD

The disclosed embodiments relate generally to compositions for alleviating food cravings, and more specifically, to compositions for daily appetite temperance, food cravings and moderation of subcutaneous triglyceride synthesis.

BACKGROUND

According to the World Health Organization, obesity rates in the general population are rapidly becoming a global concern. For example, in 2008, 1.5 billion adults were overweight (BMI>25 kg/m2). Of these, over 200 million men and nearly 300 million women were obese (BMI>30 kg/m2), while nearly 40 million children under the age of five were overweight in 2010. Further, globally obesity rates have more than doubled since 1980 from 5% to 10% in men and 8% to 14% in women. As a result, at least 2.8 million people die each year globally, as a result of being overweight or obese.

Being overweight or obese greatly increases the risk for developing a cluster of metabolic disorders, such as high blood pressure, hyperglycemia, insulin resistance, and hyperlipidemia, which, together with a few other pathophysiological abnormalities, are collectively referred to as metabolic syndrome Metabolic syndrome is a serious medical condition because it greatly increases the risks for developing devastating diseases such as T2 diabetes, coronary artery disease, stroke, atherosclerosis, fatty liver disease, and aging-related degenerative diseases.

Existing methods to control obesity, such as diets, have failed remarkably at achieving and at sustaining a proper BMI for most individuals, not to mention the continued long-term struggle endured by participants. Food craving appears to be an important construct to consider, particularly within the current food environment. Approaches that might effectively target food cravings hold significant implications for advancing public health and clinical concerns relating to overeating but have not yet come to fruition.

Therefore, a need exists to overcome the problems with the prior art as discussed above, and particularly for a more efficient way of controlling obesity.

SUMMARY

This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

The disclosed embodiments are directed to a formulation, where the appetite temperance activities of lemon essential oil, among other things, are infused within a precise proportion of gel matrix to obtain an effective appetite-suppressing topical preparation. The topical gel may relieve food cravings of various origins and moderate subcutaneous triglyceride synthesis.

The gel for topical application for alleviating food cravings is disclosed, comprising of: about 45.0 percent by weight of deionized water; about 10.0 percent by weight of benzyl alcohol; about 40.0 percent by weight of ethyl alcohol; about 0.2 percent by weight of tocopherol acetate; about 0.15 percent by weight of docosahexaenoic acid (DHA); about 1.15 percent by weight of resveratrol; about 1.0 percent by weight of a cross-linked polyacrylic acid copolymer; about 0.1 percent by weight of ethylenediaminetetraacetic acid (EDTA); about 200 µL of lemon essential oil; and, from about 100 µL to 200 µL of triethanolamine.

In another embodiment, a method of preparation of said gel for topical application for alleviating food cravings is disclosed. The method includes the steps of: dissolving deionized water in ethyl alcohol and benzyl alcohol to form a mixture; adding resveratrol to the mixture until dissolved; stirring the mixture until the resveratrol has dissolved uniformly; adding DHA to the mixture and continuing stirring of the mixture; sprinkling cross-linked polyacrylic acid copolymer onto the mixture while the mixture is stirred at about 500 rpm angular speed; adding ethylenediamine tetraacetic acid to the mixture while the mixture is stirred at about 500 rpm angular speed; adding lemon essential oil to the mixture while the mixture is stirred at about 500 rpm angular speed; adding tocopherol acetate to the mixture while the mixture is stirred at about 500 rpm angular speed; waiting at least two hours; adding triethanolamine to the mixture while the mixture is stirred at about 500 rpm angular speed and wherein aforementioned ingredients are present in the mixture following quantities:

about 45.0 percent by weight of deionized water;
about 10.0 percent by weight of benzyl alcohol;
about 40.0 percent by weight of ethyl alcohol;
about 0.2 percent by weight of tocopherol acetate;
about 0.15 percent by weight of docosahexaenoic acid (DHA);
about 1.15 percent by weight of resveratrol;
about 1.0 percent by weight of a cross-linked polyacrylic acid copolymer;
about 0.1 percent by weight of ethylenediaminetetraacetic acid (EDTA);
about 200 µL of lemon essential oil; and,
from about 100 µL to 200 µL of triethanolamine.

In another embodiment, a method for alleviating food cravings is disclosed. The method includes the steps of: periodically applying a gel topically to a user's skin, wherein said gel comprises: about 45.0 percent by weight of deionized water; about 10.0 percent by weight of benzyl alcohol; about 40.0 percent by weight of ethyl alcohol; about 0.2 percent by weight of tocopherol acetate; about 0.15 percent by weight of docosahexaenoic acid (DHA); about 1.15 percent by weight of resveratrol; about 1.0 percent by weight of a cross-linked polyacrylic acid copolymer; about 0.1 percent by weight of ethylenediaminetetraacetic acid (EDTA); about 200 μL of lemon essential oil; and, from about 100 μL to 200 μL of triethanolamine.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims. The foregoing and other features and advantages of the present invention will be apparent from the following more particular description of the preferred embodiments of the invention, as illustrated in the accompanying drawings.

BRIEF DESCRIPTION OF THE DRAWINGS

The accompanying drawings, which are incorporated in and constitute part of this specification, illustrate embodiments of the invention and together with the description, serve to explain the principles of the disclosed embodiments. The embodiments illustrated herein are presently preferred, it being understood, however, that the invention is not limited to the precise arrangements and instrumentalities shown, wherein:

FIG. 2 is a perspective view of the molecular structure of acrylate crosspolymers according to an example embodiment of the prior art;

DETAILED DESCRIPTION

Figure 1:
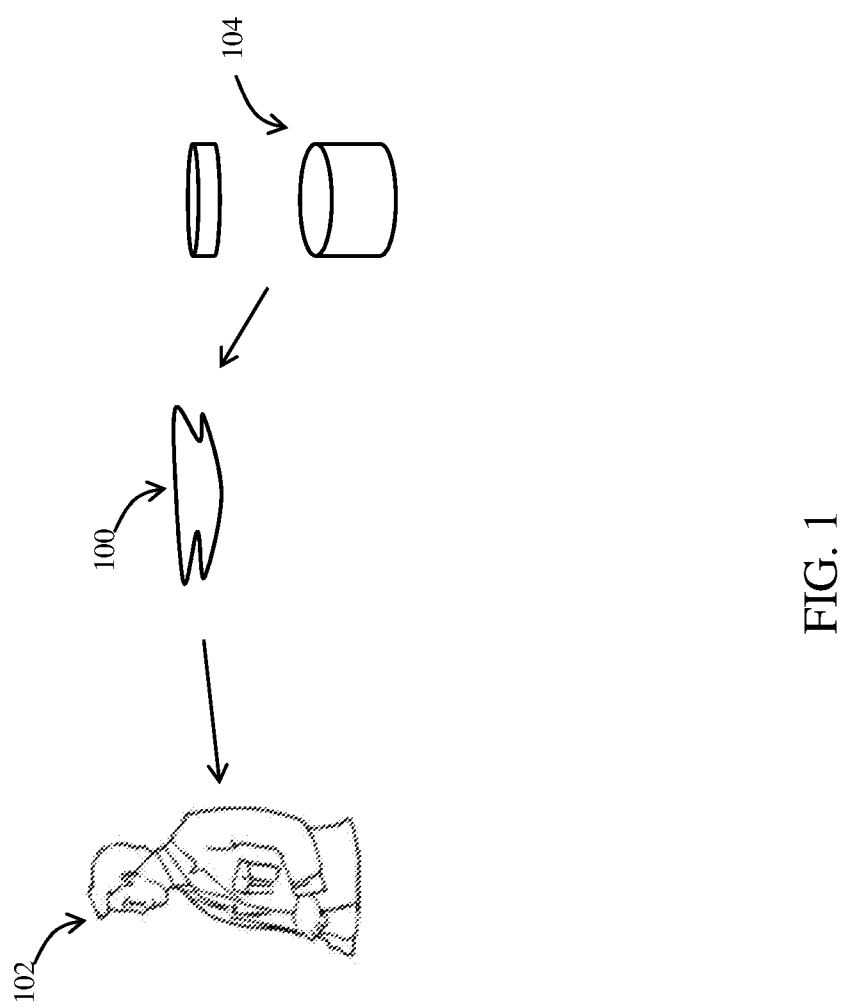
FIG. 1 is a drawing depicting a view of the claimed subject matter depicting its use.

The following detailed description refers to the accompanying drawings. Whenever possible, the same reference numbers are used in the drawings and the following description to refer to the same or similar elements. While disclosed embodiments may be described, modifications, adaptations, and other implementations are possible. For example, substitutions, additions or modifications may be made to the elements illustrated in the drawings, and the methods described herein may be modified by substituting reordering or adding additional stages or components to the disclosed methods and devices. Accordingly, the following detailed description does not limit the disclosed embodiments. Instead, the proper scope of the disclosed embodiments is defined by the appended claims.

The disclosed embodiments provide methods for losing excessive body weight and reaching healthier Body Mass Index ratio (BMI) via treatment protocols for alleviating food cravings. The claimed subject matter improves over the prior art by providing methods of preparation and application of a topical gel configured for promotion of daily appetite temperance and high glycemic food cravings suppression along with moderation and/or reduction of subcutaneous triglyceride synthesis. The disclosed gel and treatment protocol reduces or alleviates food cravings by providing appetite temperance via the application of the topical gel to the skin of a user, which may increase the success rate for the user in reducing overeating or promoting a moderate or reduced appetite, and as a result may reduce the risk factors associated with obesity.

The disclosed embodiments further include additional health benefits. One particular study found that leptin deficiency also contributes to the development of progressive insulin resistance and associated neuroendocrine derangements in uDM (Diabetes Mellitus). The study found that systemic administration of exogenous leptin at a dose that maintains normal physiologic plasma leptin levels prevented the development of severe, progressive insulin resistance in rats with uDM and that this effect could not be explained by leptin induced changes in food intake or body weight. Therefore, the restoration of leptin signaling restores insulin signaling, alleviating any insulin resistance and maintaining systemic glucose homeostasis. Consequently, the disclosed embodiments aid in treating insulin resistance.

Another study involved the type of neurons having Leptin Receptors (Lepr) in the hypothalamus (Dorsomedial Hypothalamic nucleus or DMH) that activate thermogenesis. The study found that a defined single population of first-order neuron is critical for leptin's actions on adaptive thermogenesis. PrRP neurons in the DMH are sensitive to energy status, possess Lepr, and respond to stimulation by leptin. As all of leptin's effects on metabolism are mediated by brain-expressed Lep. The study also demonstrates that PrRP signaling itself is central to the leptin pathway mediating thermogenesis. With PrRP knock-out mice, their body weights diverge significantly from wild-type littermates within 2 weeks of the change in diet. The former meaning that in mice genetically modified not to express PrRP neurons, the study shows that reduced thermogenesis reflects on increased weight gain, confirming PrRP signaling as central. The restoration of proper BMI not only gets achieved by decreased calorie ingestion following diminishment of craving of high glycemic foods and general appetite reduction, but also by restoration of proper thermogenesis expenditure of energy. Consequently, the disclosed embodiments aid thermogenesis expenditure of energy.

2-Arachidonoylglycerol (2-AG), an endocannabinoid agonist for the Cannabinoid receptor Type 1 (CB1r), is a hormone secreted by adipose tissue, which is ultimately eliminated through two-step process consisting of carrier-mediated transport into cells and subsequent enzymatic hydrolysis. Hsp70 proteins transport 2-AG inside the cytosol and binds 2-AG resulting in inactivation of signaling to CB1r. If upregulation occurs, then signaling will be temperate and appetite will decrease. Leptin is a hormone predominantly made by adipose cells and enterocytes in the small intestine that helps to regulate energy balance by inhibiting hunger, which in turn diminishes fat storage in adipocytes. A study from Franco et al. confirms that resveratrol, a phytoalexin, normalizes leptin resistance by preventing the development of central leptin resistance. Hence, creating a therapeutic tool for treating obesity.

FIG. 1 is a view of the disclosed embodiments depicting its use via application of a composition 100 to a user 102. In one embodiment, composition 100 may be a colloid that is substantially by weight of liquid, which is immobilized by surface tension between composition 100 and a macromolecular network of fibers built from a small amount of carbomer or any other applicable gelatin aqueous based substance. In one embodiment, composition 100 is manifested via c10-30 alkyl acrylate crosspolymer or any other applicable substance including a thickening efficiency, suspending capability, and long viscous flow. Composition 100 may be housed in a reservoir 104. The reservoir 104 may be comprised of material such as carbon steel, stainless steel, aluminum, Titanium, other metals or alloys, composites, ceramics, polymeric materials such as polycarbonates, such as Acrylonitrile butadiene styrene (ABS plastic), Lexan™, and Makrolon™, and the like. The reservoir 104 may be formed from a single piece or from several individual pieces joined or coupled together. The components of reservoir 104 may be manufactured from a variety of different processes including an extrusion process, a mold, welding, shearing, punching welding, folding etc. The user 102 applies an effective amount of composition 100 to a skin surface in a distributed manner allowing the gel to be evenly applied. An effective amount is defined as an amount that easily fits on the finger or hand of user 102 and is configured to cover one or more targeted areas configured for effective ingestion by the user 102. In one embodiment, composition 100 may be ingested into user 102 by inhaling, consuming, or any other applicable method for ingesting a substance configured to be consumed, and ingestion may occur periodically, daily, or any other defined period of time based on factors associated with the user 102. The amount of composition 100 applied to user 102 for ingestion may vary depending on factors associated with user 102 including but not limited to, weight, height, BMI, metabolism, muscle mass, energy consumption levels, diet, or any other applicable factor.

As used herein the following terms are intended to have meaning as follows: namely, "mixture", "composition", and "formulation" meaning pharmaceutical compositions formulated and compounded with a topical gel matrix. "Gel" or "gel matrix" meaning a colloid that is basically 99% by weight of liquid which is immobilized by surface tension between it and macromolecular network of fibers built from a small amount of a substance gelating material present. Gel or gel matrix may include Carbopol® Aqua CC polymer/acrylate crosspolymer, and the like. As used herein, "acrylate crosspolymer" may be intended to mean "Carbopol® Aqua CC polymer".

In one embodiment, composition 100 may include pine oil essential oil or pine oil extract, and ethyl alcohol ($C_2H_5OH$) in order to provide reliable molecule transfer and clearance to the skin of user 102. In one embodiment, the ethyl alcohol is of 40% volume in order to provide permeation functionality to composition 100 for the skin of user 102. In one embodiment, composition 100 may include a plurality of herbs and/or vitamins in order to contribute or enhance the therapeutic functions of the composition 100 when applied to the skin of user 102. In one embodiment, composition 100 may include one or more permeation enhancing components configured to assist in the effectiveness of the application of composition 100.

All pharmaceutical compositions and dosage forms for application of composition 100 to the skin are contemplated by the invention, including topical patch, transdermal patch, plaster, pastes, gel, liposomes, a liquid, semisolid, solution, suspension, lotion, cream, ointment, foam, sprayable aerosol, sprayable non-aerosol, provided they include (i) a releasable or substantially releasable cannabinoid agonist; and (ii) a non-releasable or substantially non-releasable aversive agent selected from cannabinoid antagonists, or mixtures thereof.

Referring now to FIG. 2, composition 100 may be prepared utilizing a polymerizable material 200 such as a multifunctional acrylic acid ($CH_2$), metacrylic acid ($C_4H_6O_2$), polyacrylic acid ($C_3H_4O_2$)$_n$, or ester. In one embodiment, composition 100 may include processing aids such as water-soluble or water-dispersible polymers having anionic, cationic, zwitterionic, or ionic character. Acrylate crosspolymers are rheology modifiers, cross-linked polyacrylic acid for thickening, suspending, and as a stabilizer agent used in a wide variety of personal care products. It delivers excellent thickening efficiency and suspending capability, long viscous flow and sparkling clarity in gel systems. It is characterized by dispersing and "swelling" in aqueous media, forming gels and sols displaying fairly high viscosity. These qualities integrate more stable and clear as well as gelling properties, perfectly contrasted against pH. Crosslinked alkyl acrylates are reported to function as absorbents, film formers, emulsion stabilizers, viscosity increasing agents, suspending agents, binders, and/or skin conditioning agents in cosmetic formulations. Acrylate copolymer is a general term for copolymers of two or more monomers consisting of acrylic acid, methacrylic acid or one of their simple esters as represented by the structures 200 shown in FIG. 2. The gel of the disclosed embodiments comprises about 0.3 percent by weight of acrylate crosspolymer. In an embodiment where 100 grams of said gel are produced, the gel of the disclosed embodiments comprises about 0.3 grams of acrylate crosspolymer.

In addition, Carbopol® Aqua CC polymer may also comprise: amino substituents, which provide hydrophilicity and cationic properties at low pH; hydrophobic substituents which moderate the hydrophilicity; hydrophobically modified polyoxyalkylene substituents which provide associative properties; crosslinker—the unique design of this polymer features an optimized balance of hydrophilic and hydrophobic character, with amine functionality which further activates ionic (cationic) characteristics at low pH (in use). Importantly, the polymer incorporates a proprietary modified hydrophobe package which enables controlled associative thickening and provides enhanced rheological properties.

Figure 3:
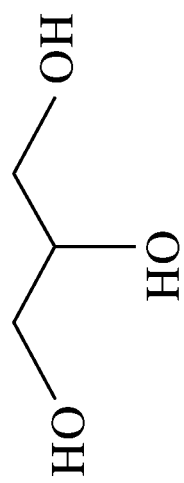
FIG. 3 is a perspective view of the molecular structure of glycerin according to an example embodiment of the prior art.

Referring now to FIG. 3, composition 100 may be prepared utilizing glycerol ($C_3H_8O_3$) 300 and/or a polymer of glycerol in order to provide humectant properties. References to glycerol 300 shall be understood to include derivatives of glycerol. "Glycerin" meaning "Gliceryn," "Glycerol," "Glycerine," "1,2,3-Propanetriol," "Glyceritol," "Glycyl alcohol," "Trihydroxypropane," "Propanetriol," "Osmoglyn," and "1,2,3-trihydroxypropane" is a trihydroxy sugar alcohol with three hydroxyl groups that are responsible for its solubility in water and its hygroscopic nature and may function in the composition as humectant, improving smoothness, providing lubrication, emollient agent, skin conditioning agent, skin protector, and viscosity decreasing agent as represented by the structure 300 shown in FIG. 3.

Glycerin is widely used as humectantin cosmetics and personal care products, also as hair conditioning agent, in skin creams and lotions, in shaving preparations, deodorants, make up, oral care agent, skin conditioning agent, and viscosity decreasing agents. Glycerine is virtually nontoxic, non-irritating, and odorless. It functions as a humectant, vehicle, and emollient. The U.S. Food and Drug Administration (FDA) includes glycerin on its list of direct food additives considered Generally Recognized As Safe (GRAS), and on its list of approved indirect food additives. Glycerin is also an FDA approved active ingredient in Over-the-Counter (OTC) skin protectant drug products, ear drying products and it an approved demulcent for the eyes. Glycerin in the formulation is required such as humectants and emollient agent, skin conditioning agent, skin protector, and viscosity decreasing agents. The gel for the present formulation comprises about 0.05 percent by weight of glycerin. In an embodiment where 100 grams of said gel are produced, the gel of the disclosed embodiments comprises about 0.5 grams of glycerin.

"Deionized water" meaning "demineralized water"/"DM water", "DI water", "DIW" or "de-ionized water"), is water that has had almost all of its mineral ions removed, such as cations like sodium, calcium, iron, and copper, and anions such as chloride and sulfate. "Deionized water" meaning water that is treated with a chelating agent such as tetrasodium ethylenediamine tetraacetic acid or tetrasodium EDTA. Deionized water prevents the clarity and viscosity from being negatively affected due to carbopol polymers' sensitivity to hard water ions. The gel of the disclosed embodiments comprises about 45.0 percent by weight of deionized water. In an embodiment where 100 grams of said gel are produced, the gel of the disclosed embodiments comprises about 45 grams of deionized water.

Figure 4:
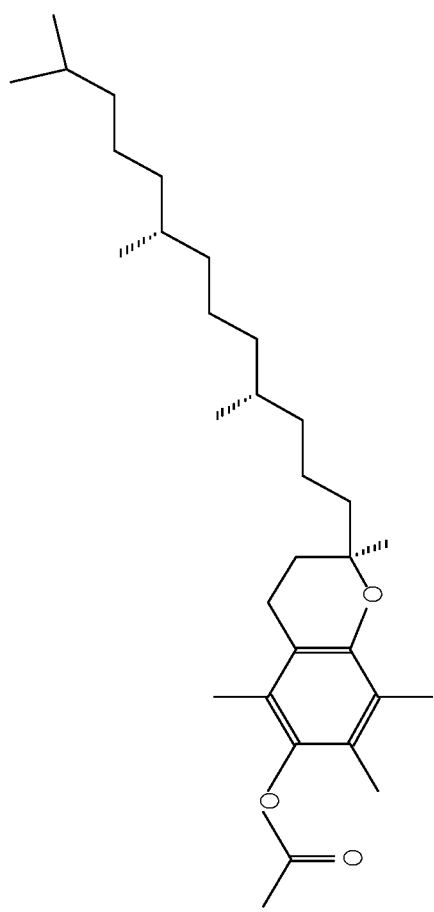
FIG. 4 is a perspective view of the molecular structure of tocopheryl acetate according to an example embodiment of the prior art.

Referring now to FIG. 4, composition 100 may include tocopheryl acetate ($C_{31}H_{52}O_3$) 400, also known as 2H-1-Benzopyran-6-ol, 3,4-dihydro-2,5,7,8-tetramethyl-2-(4,8,12-trimethyltridecyl)-, acetate; 3,4-Dihydro-2,5,7,8-tetramethyl-2-(4,8,12 trimethyltridecyl)-2H-b-enzopyran-6-ol, acetate; DL-alpha tocopheryl acetate; or Vitamin E acetate providing both an antioxidant and skin conditioning agent. "Tocopherol acetate" meaning "tocopheryl acetate," "vitamin E acetate," "DL-alpha-tocopheryl acetate," "ephynal," "syntopherol acetate," and "rovimix E 50SD" is a collective name for a group of closely related lipids that contain substitutions on the 2H-1-benzopyran-6-ol nucleus and a long hydrocarbon chain of isoprenoid units may function in the formulation as an antioxidant and skin conditioning agent, as represented by the structure 400 shown in FIG. 4. Tocopherol acetate is a powerful antioxidant that helps to protect cell membranes, making it a great ingredient as a dry skin protector agent. The CIR Expert Panel evaluated the scientific data and concluded that tocopherol and the related ingredients were safe as used in cosmetics and personal care products. Tocopherol acetate in the formulation is required such as an antioxidant and skin conditioning agent. The gel of the disclosed embodiments comprises about 0.2 percent by weight of tocopherol acetate. In an embodiment where 100 grams of said gel are produced, the gel of the disclosed embodiments comprises about 0.2 grams of tocopherol acetate.

Figure 5A:
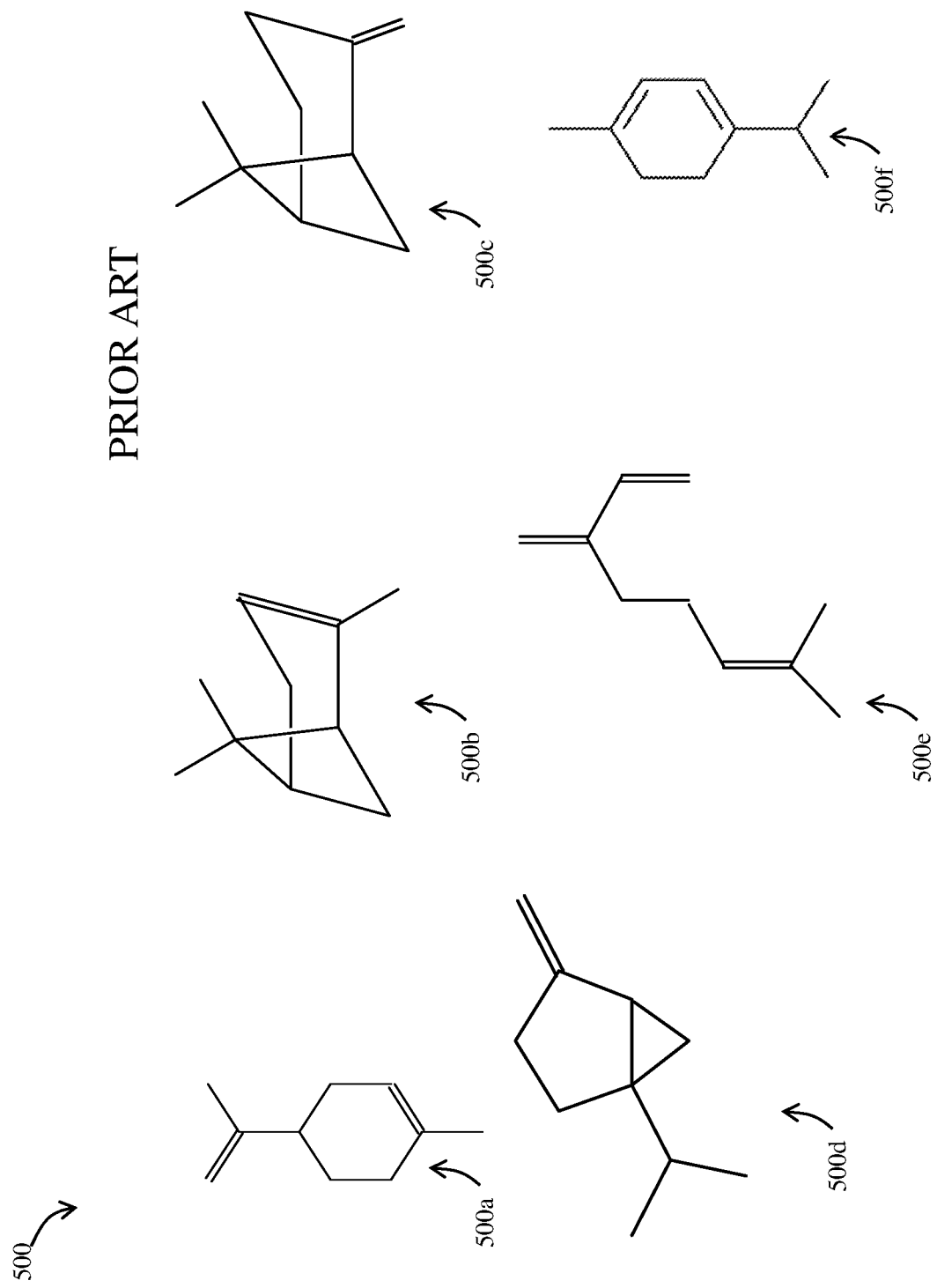
FIGS. 5A-B are perspective views of the molecular structure of various terpenes of lemon essential oil.
Figure 5B:
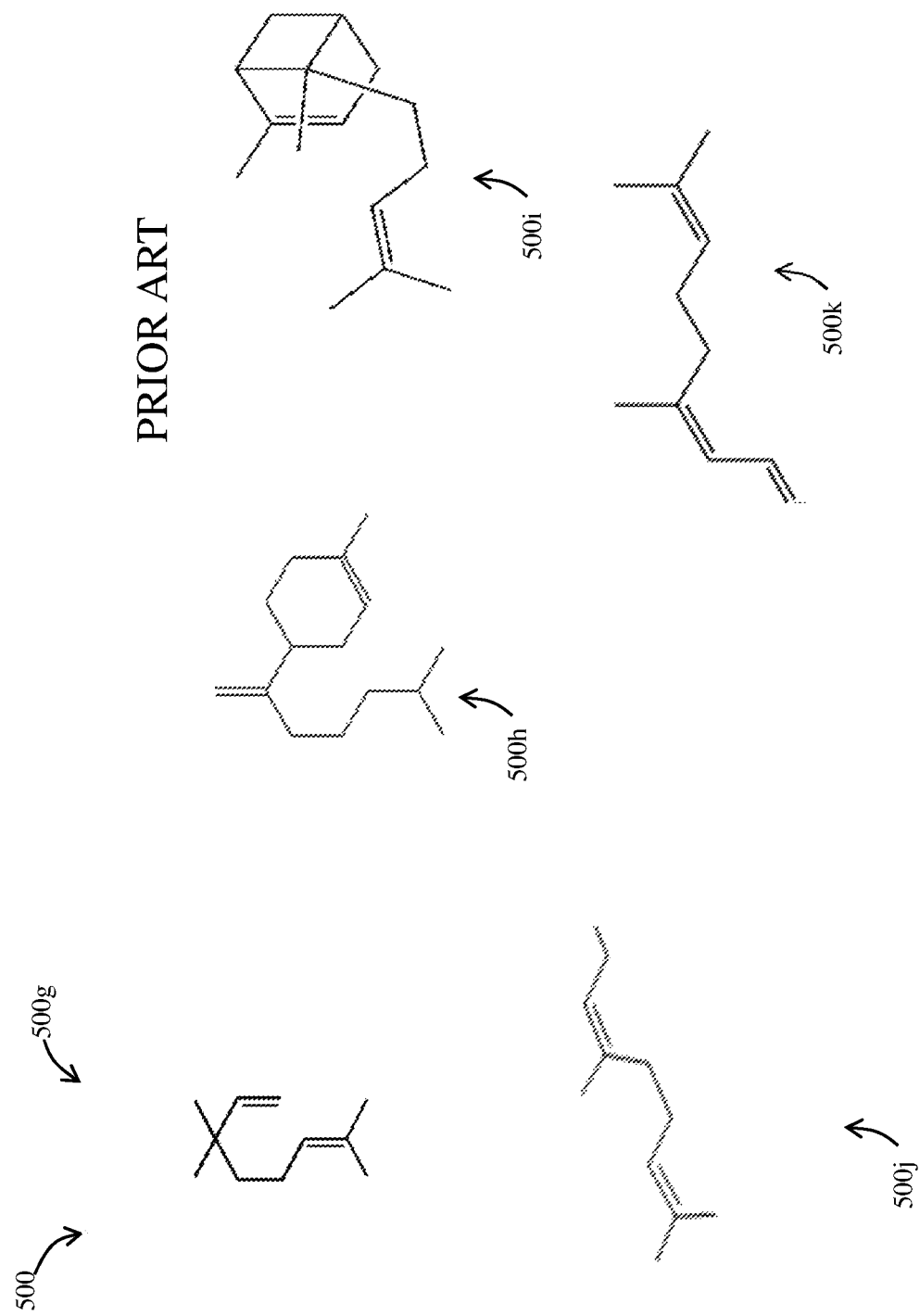

"Lemon essential oil" is an aromatic liquid that contains the principal components of lemon oil configured to include stimulating, calming, astringent, detoxifying, antiseptic, disinfectant, and anti-fungal properties. FIGS. 5A-B are perspective views of the molecular structures 500 of various terpenes of lemon essential oil; 500a is the molecular structure for limonene; 500b is the molecular structure for alpha pinene; 500c is the molecular structure for beta pinene; 500d is the molecular structure for sabinene; 500e is the molecular structure for myrcene; 500f is the molecular structure for alpha terpinene; 500g is the molecular structure for linalool; 500h is the molecular structure for beta bisabolene; 500i is the molecular structure for trans alpha bergamotene; 500j is the molecular structure for nerol; and 500k is the molecular structure for neral. The lemon essential oil may function in the composition as a fragrance or perfuming agent. In one embodiment, the lemon essential oil is about 2.00 percent by weight of the total composition (200 µL). In an embodiment where 100 grams of said gel are produced, the gel of the disclosed embodiments comprises about 2 grams of lemon essential oil.

Figure 6:
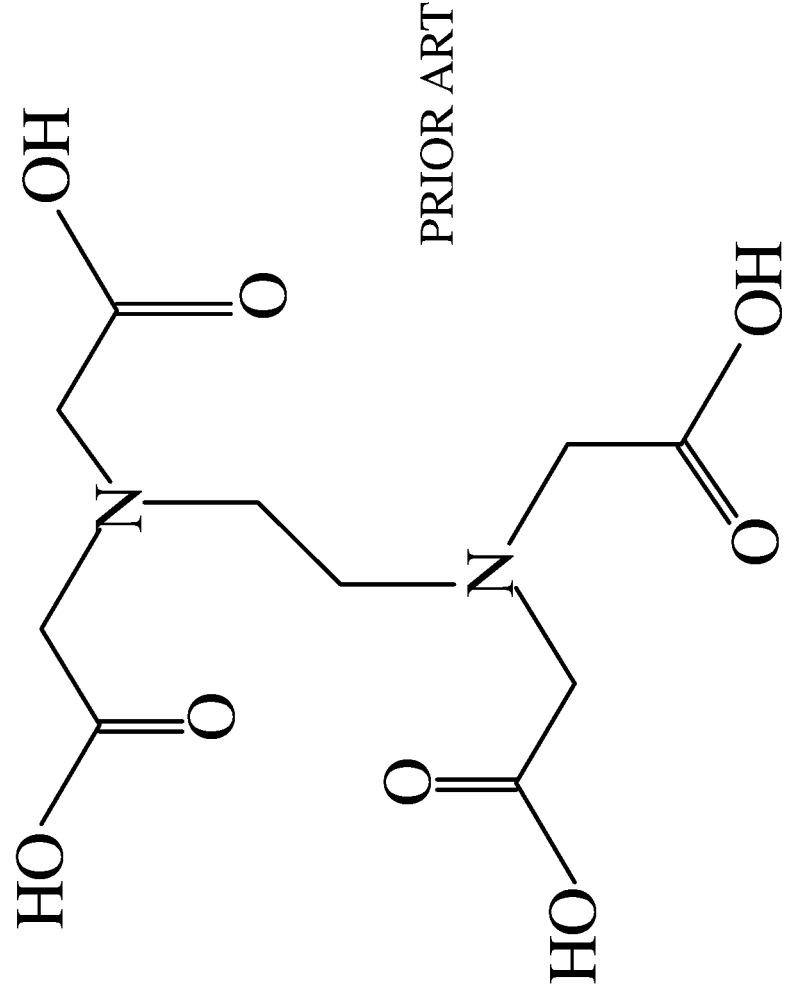
FIG. 6 is a perspective view of the molecular structure of ethylenediamine tetraacetic acid according to an example embodiment of the prior art.

Referring now to FIG. 6, composition 100 may include ethylenediaminetetraacetic acid ($C_{10}H_{16}N_2O_8$) 600 or any applicable pharmaceutically acceptable salt of ethylenediaminetetraacetic or derivatives thereof in order to serve as a chelating agent for complexing metal ions. "Ethylenediamine tetraacetic acid" (EDTA) and its salts are crystalline powders often used in cosmetics and personal care products. EDTA is included in the formulation to stabilize the Carbopol® gel. If metal ions are present, they can depolymerize the carbopol with loss in viscosity, and therefore, the instability of the emulsion. EDTA is used to bind of metal ions to prevent the deterioration of formulation. It also helps to maintain clarity, protect fragrance compounds, and prevent rancidity. In one embodiment, ethylenediaminetetraacetic acid 600 (EDTA) or combination of chelating agents is stirred into composition 100 at about 500 rpm angular speed, and accounts for about 0.10% of the weight of composition 100 based on the total weight of the aqueous gel.

Figure 7:
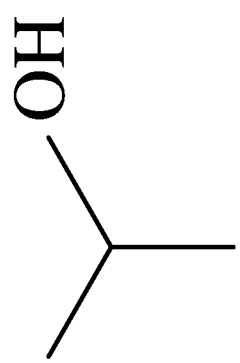
FIG. 7 is a perspective view of the molecular structure of isopropyl alcohol according to an example embodiment of the prior art.

Referring now to FIG. 7, composition 100 may include benzyl alcohol ($C_6H_5CH_2OH$) 700, isopropyl alcohol (C3H8O), ethyl alcohol (CH3CH2OH), or any other applicable lower alkyl alcohol. "Isopropyl alcohol" meaning "2-propanol," "isopropanol," "isopropyl alcohol," "propan-2-ol," "sec-propyl alcohol," "2-hydroxypropane," and "dimethylcarbinol" is a widely used ingredient in cosmetics and personal care products and kills and prevents growth of microorganisms. Isopropyl alcohol is an alcohol that evaporates quickly. Isopropyl alcohol is a widely used ingredient in cosmetics and personal care products and can be found in products such as aftershave lotions, bath products, eye makeup, other makeup products, cleansing products, as well as nail, hair and skin care products. Isopropyl alcohol is used to dissolve other substances in cosmetics and personal care products. It is also used to decrease the thickness of liquids and to reduce the tendency of finished products to generate foam when shaken. Isopropyl alcohol has an odor resembling ethanol and it has a slightly bitter taste. Isopropyl alcohol is volatile and produces a cooling effect upon evaporation. Rubbing alcohol consists primarily of isopropyl alcohol. Isopropyl alcohol kills and prevents the growth of microorganisms. Isopropyl alcohol in the formulation is required to dissolve the lemon essential oil and other ingredients and to provide cooling effect upon evaporation. Also it is necessary as solvent and to decrease the thickness. Furthermore it prevents the growth of microorganisms. In one embodiment, benzyl alcohol 700 accounts for approximately 10% of the weight of composition 100 and functions as a permeation enhancement for composition 100, and ethyl alcohol accounts for approximately 40% of the weight of composition 100 and functions as not only a permeation enhancer and inhibition agent of micro-organism growth, but also a solvent and cooling agent.

Figure 8:
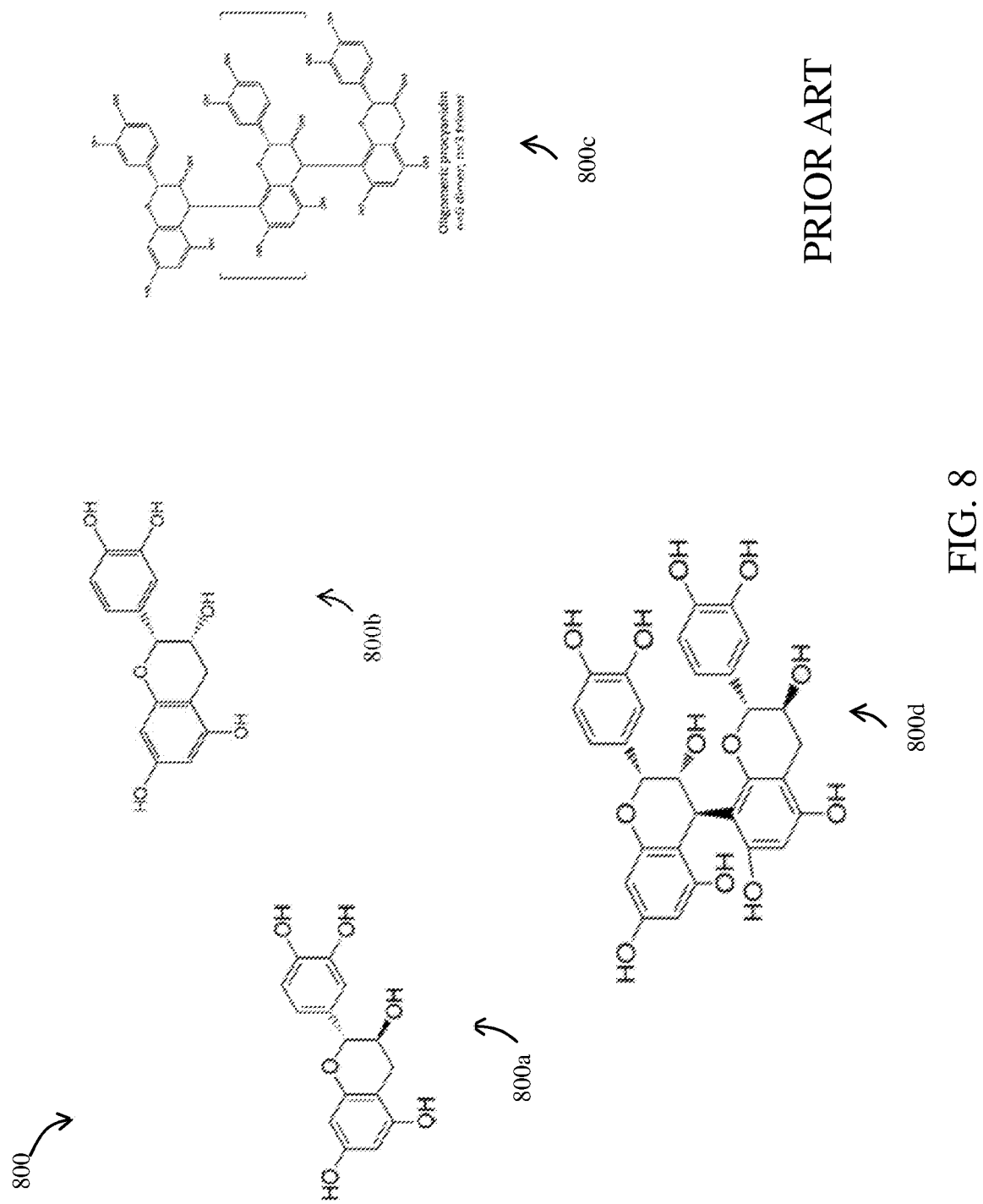
FIG. 8 is a perspective view of the molecular structure of epicatechin, catechin, oligomeric procyanidin, and procyanidin dimer b1 according to an example embodiment of the prior art.

Referring now to FIG. 8, composition 100 may include nutritional components containing docosahexaenoic acid (DHA) or any other applicable omega-3 fatty acids. DHA is configured to treat proteins and powerfully upregulate HSP70 expression and in application to composition 100 is configured to promote HSP70. Consumption of DHA by user 102 via the application of composition 100 may include a simultaneously intake of proanthocyanidins, which include but are not limited to flavan-3-ols and polymers of flavan-3-ols including but not limited to epicatechin ($C_{15}H_{14}O_6$) 800a, catechin ($C_{15}H_{14}O_6$) 800b, oligomeric procyanidin ($C_{31}H_{28}O_{12}$) 800c, procyanidin dimer b1 (C30H26O12) 800d, and/or any other applicable flavonoids configured to enhance brain function. In one embodiment, DHA is configured to account for 0.15% of the weight of composition 100. In one embodiment, DHA is added to composition 100 during a continuous stir once a uniform dissolution of the composition 100 has been achieved.

Figure 9:
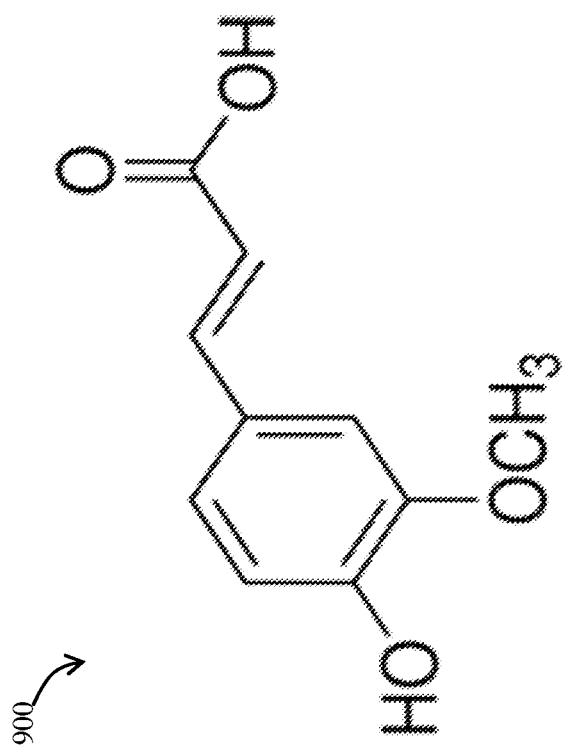
FIG. 9 is a perspective view of the molecular structure of ferulic acid according to an example embodiment of the prior art.

In one embodiment, composition 100 may include ferulic acid or a derivative of ferulic acid as represented by the structure 900 shown in FIG. 9 configured to be solubilized by the ethyl alcohol in order to provide reliable molecule transfer and clearance to the skin of user 102. Ferulic acid serves as an antioxidant-boosting skin care ingredient configured to fight off free radicals and boost the effects of other antioxidants. In one embodiment, ferulic acid and lemon essential oil function as a mechanism to enhance the delivery of the active ingredients in composition 100.

Figure 10:
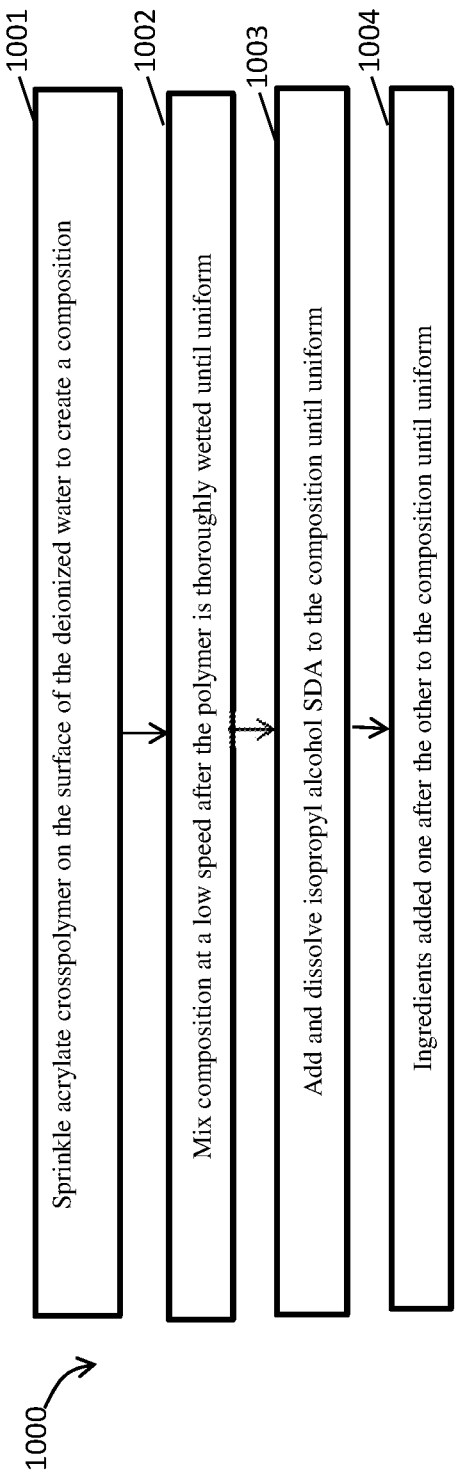
FIG. 10 is a block diagram that depicts a method of preparation of a gel for topical application for alleviating food cravings according to an example embodiment; and, FIG. 11 is a table of physical properties of a topical gel for alleviating food cravings, according to an example embodiment.

Referring now to FIG. 10, is a block diagram depicting a process 1000 for preparing composition 100 configured for topical application for alleviating food cravings. At block 1201, an acrylate crosspolymer is sprinkled on the surface of a plurality of deionized water configured to function as a diluent. In one embodiment, the plurality of deionized water may be dissolved in appropriate quantities to ethyl alcohol and benzyl alcohol generating a composition or mixture. In one embodiment, the deionized water accounts for about 45%, benzyl alcohol accounts for about 10%, and ethyl alcohol accounts for 40% of the weight of composition 100. At block 1002, the mixture or composition is mixed or stirred at a low speed until the mixture is uniform. In one embodiment, the composition becomes uniform after the polymer is thoroughly wetted in which the composition is subsequently mixed. At block 1003, isopropyl alcohol is added and dissolved into the composition until the mixture is uniform. At block 1004, the following ingredients are added to the mixture in order to render composition 100, said ingredients are not required to be added to the mixture in a particular order; however, during the addition of said ingredients the mixture is constantly and continuously stirred. In one embodiment, the constant and continuous stirring is accomplished at 500 rpm angular speed which is configured to be maintained during the entire process 1000. In one embodiment, resveratrol is slowly added to the mixture and allowed to dissolve functioning as an antioxidant in composition 100. Resveratrol is stirred into the mixture until a uniform dissolution has been achieved. The resveratrol accounts for about 1.15% of the weight of composition 100. DHA is added to the mixture functioning as a promoter of HSP70 in composition 100. Lubrizol ETD 2020 or any other applicable polymer is sprinkled slowly into the mixture. In one embodiment, the Lubrizol ETD 2020 accounts for about 1% of the weight of composition 100 and is configured to function as a rheology modifier allowing for efficient flow. Ethylenediaminetetraacetic acid (EDTA) is added to the mixture and configured to function as a chelating agent. In one embodiment, EDTA accounts for 0.10 of the weight of composition 100. Tocopheryl acetate is added to the mixture as an antioxidant and skin conditioning agent. In one embodiment, tocopheryl acetate may account for approximately 0.20% of the weight of composition 100. In one embodiment, the Lubrizol ETD 2020 occupies the mixture for at least 2 hours allowing a complete wetting action to be achieved. After the wetting action is completed, Triethanolamine is added to the fixture as needed in order to function as a PH neutralizing agent allowing the composition of mixture. In one embodiment, about 200 μL of lemon essential oil or any other applicable essential oil may be added to the mixture for purpose of providing a fragrance to composition 100. Upon mixture of the aforementioned ingredients, the mixture or composition is able to render the final product of composition 100. In one embodiment, the pH of composition 100 once the Triethanolamine is added is approximately between 5.5 to 6.

Referring now to FIG. 11, table of physical properties of composition 100 for alleviating food cravings is illustrated. Upon completion of the entire mixture, composition 100 is configured to be stabilized via a storage time of 3 month at an approximate temperature of 45 degrees C. In one embodiment, composition 100 is configured to endure approximately 5 cycles of freezing and thawing. In one embodiment, the viscosity level is approximately between 6,000-14,000 mPa, the pH level of composition 100 after stabilization is approximately between 5.5 and 6, the yield value is approximately between 1000-2000 (dyn/cm2), and the turbidity level of composition 100 is greater than 20 NTU (Nephelometric Turbidity Units).

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

I claim:

1. A gel for topical application for alleviating food cravings, comprising of:
   about 45.0 percent by weight of deionized water;
   about 10.0 percent by weight of benzyl alcohol;
   about 40.0 percent by weight of ethyl alcohol;
   about 0.2 percent by weight of tocopherol acetate;
   about 0.15 percent by weight of docosahexaenoic acid (DHA);
   about 1.15 percent by weight of resveratrol;
   about 1.0 percent by weight of a cross-linked polyacrylic acid copolymer;
   about 0.1 percent by weight of ethylenediaminetetraacetic acid (EDTA);
   about 200 μL of lemon essential oil; and,
   from about 100 μL to 200 μL of triethanolamine.

2. The gel of claim 1, wherein the gel further comprises a viscosity in the range of approximately 6.000 to 14.000 millipascal-second.

3. The gel of claim 1, wherein the gel further comprises a pH in the range of approximately 5.5 to approximately 6.

4. The gel of claim 1, wherein the gel further comprises a turbidity approximately greater than 20 nephelometric turbidity units.

5. A method for preparing a gel for topical application for alleviating food cravings, comprising the steps of:
   dissolving deionized water in ethyl alcohol and benzyl alcohol to form a mixture;
   adding resveratrol to the mixture until dissolved;
   stirring the mixture until the resveratrol has dissolved uniformly;

adding DHA to the mixture and continuing stirring of the mixture;
sprinkling cross-linked polyacrylic acid copolymer onto the mixture while the mixture is stirred at about 500 rpm angular speed;
adding ethylenediaminetetraacetic acid to the mixture while the mixture is stirred at about 500 rpm angular speed;
adding lemon essential oil to the mixture while the mixture is stirred at about 500 rpm angular speed;
adding tocopherol acetate to the mixture while the mixture is stirred at about 500 rpm angular speed;
waiting at least two hours;
adding triethanolamine to the mixture while the mixture is stirred at about 500 rpm angular speed until a mixture viscosity of 6.000 to 14.000 mPa and a pH of 6 is attained; and
wherein aforementioned ingredients are present in the mixture in the following quantities:
about 45.0 percent by weight of deionized water;
about 10.0 percent by weight of benzyl alcohol;
about 40.0 percent by weight of ethyl alcohol;
about 0.2 percent by weight of tocopherol acetate;
about 0.15 percent by weight of docosahexaenoic acid (DHA);
about 1.15 percent by weight of resveratrol;
about 1.0 percent by weight of a cross-linked polyacrylic acid copolymer;
about 0.1 percent by weight of ethylenediaminetetraacetic acid (EDTA);
about 200 µL of lemon essential oil; and,
from about 100 µL to 200 µL of triethanolamine.

6. The method of claim 5, wherein the mixture comprises a viscosity in the range of approximately 6.000 to 14.000 millipascal-second.

7. The method of claim 5, wherein the mixture further comprises a turbidity approximately greater than 20 nephelometric turbidity units.

8. The method of claim 5, further comprising storing the mixture at a temperature of at least 45° C. for a plurality of months.

9. A method for alleviating food cravings, comprising the steps of:
periodically applying a gel topically to a user's skin, wherein said gel comprises:
about 45.0 percent by weight of deionized water;
about 10.0 percent by weight of benzyl alcohol;
about 40.0 percent by weight of ethyl alcohol;
about 0.2 percent by weight of tocopherol acetate;
about 0.15 percent by weight of docosahexaenoic acid (DHA);
about 1.15 percent by weight of resveratrol;
about 1.0 percent by weight of a cross-linked polyacrylic acid copolymer;
about 0.1 percent by weight of ethylenediaminetetraacetic acid (EDTA);
about 200 µL of lemon essential oil; and,
from about 100 µL to 200 µL of triethanolamine.

10. The method of claim 9, wherein the gel comprises a viscosity in the range of approximately 6.000 to 14.000 millipascal-second.

11. The method of claim 9, wherein the gel comprises a pH in the range of approximately 5.5 to approximately 6.

12. The method of claim 9, wherein the gel further comprises a turbidity approximately greater than 20 nephelometric turbidity units.

\* \* \* \* \*